United States Patent [19]

Zick et al.

[11] 4,450,842

[45] May 29, 1984

[54] SOLID STATE REFERENCE ELECTRODE

[75] Inventors: Gregory L. Zick, Seattle, Wash.; Stanley H. Saulson, Miami, Fla.

[73] Assignee: Cordis Corporation, Miami, Fla.

[21] Appl. No.: 318,693

[22] Filed: Nov. 6, 1981

Related U.S. Application Data

[63] Continuation of Ser. No. 143,927, Apr. 25, 1980, abandoned.

[51] Int. Cl.$^3$ .............................................. A61B 5/00
[52] U.S. Cl. .................................. 128/635; 204/403; 204/415; 204/431
[58] Field of Search ............... 128/635, 632, 639–641, 128/644; 204/195 B, 195 P, 403, 415, 431–433

[56] References Cited

U.S. PATENT DOCUMENTS

| | | | |
|---|---|---|---|
| 3,399,667 | 9/1968 | Nishimoto et al. | 128/635 X |
| 3,662,745 | 5/1972 | Cosentino | 128/635 |
| 3,795,239 | 3/1974 | Eberhard et al. | 128/635 |
| 4,148,305 | 4/1979 | Reichenberger | 128/635 |
| 4,270,543 | 6/1981 | Tabuchi et al. | 128/639 |
| 4,324,257 | 4/1982 | Albarda | 128/635 |

OTHER PUBLICATIONS

Piraino et al., "An Instrumentation System . . . ", Oct. 6–7, 1979 IEEE, pp. 55–58.

Enhancing Oxygen Electrode Stability with Plasma Polymerized Coatings—Allen W. Hahn et al.

J. Appl. Phys., vol. 49, No. 10, Oct. 1978—*Adhesion and Hydrophilicity of Glow–Discharge–Polymerized Propylene Coatings*—Ashtok K. Sharma et al.

24th ACEMB-International Hotel, Las Vegas, Nev.—Oct. 31-Nov. 4, 1971—*Cold Plasma Polymerized Films and Their Biomedical Appln.*—Mayhan & Hahn.

IEEE Transactions on Parts, Materials and Packaging, vol. PMP-5, No. 2, Jun. 1969—*Organic Thin-Film Capacitor*—Paul J. Ozawa.

*Primary Examiner*—Lee S. Cohen
*Attorney, Agent, or Firm*—Kenway & Jenney

[57] ABSTRACT

In the reference electrode construction disclosed herein, silver and silver chloride particles are incorporated in a mixture including a fusible glass frit. After being printed on a suitable substrate, the mixture is fired to bond the silver/silver chloride composite into a conductive film on the surface of the substrate.

7 Claims, 6 Drawing Figures

SOLID STATE REFERENCE ELECTRODE

This is a continuation of application Ser. No. 143,927, filed Apr. 25, 1980, now abandoned.

BACKGROUND OF THE INVENTION

This invention relates to the construction of a polarographic reference electrode suitable for use in a system for measuring the partial pressure of oxygen in a patient's blood. The electrode is particularly adapted for use in the oxygen sensing system disclosed in the copending application of Gregory Zick entitled Oxygen Sensing, being filed of even date herewith.

The reference electrode of the present invention is generally of the silver/silver chloride type. Earlier efforts at forming silver/silver chloride reference electrodes have largely involved the in situ chloridation of pure silver by a wet electrolytic process. In general, these processes have been difficult to control and the resultant electrodes have not evidenced satisfactory stability in providing a reference potential for polarographic purposes.

An object of both said copending application and the present invention is the provision of a solid state sensor for use in transcutaneous oxygen sensing. The present invention pertains principally to the provision of an improved reference electrode for use in such a sensor.

Among the several objects of the present invention are the provision of a reference electrode which can be constructed using thick film fabrication techniques; the provision of a reference electrode which will provide a highly stable reference potential; the provision of a reference electrode which will facilitate accurate measurement of blood oxygen content by polarographic techniques; the provision of a reference electrode construction which is relatively simple and inexpensive. Other objects and features will be in part apparent and, in part, pointed out hereinafter.

SUMMARY OF THE INVENTION

Briefly, the practice of the present invention involves the mixing of silver and silver chloride particles together with a fusible glass frit. The mixture is then printed on a substrate in a suitable pattern and fired so as to form a conductive film bond on the surface of the substrate.

In accordance with preferred practice of the invention, a thin flat ceramic substrate is provided having front and back surfaces, the front surface being adapted to contact a patient's skin. A noble metal cathode extends through the substrate to the front surface where a limited area is exposed for reducing oxygen. A reference electrode comprising the mixture of silver and silver chloride particles in a fusible glass frit binder is printed on the front surface adjacent the cathode. A resistor is printed onto the back surface of the substrate for heating the substrate. A polymer coating, formed in situ by plasma polymerization, is provided over the front surface of the substrate, including the electrodes.

BRIEF DESCRIPTION OF THE DRAWINGS

Corresponding reference characters indicate corresponding parts throughout the several views of the drawings.

DESCRIPTION OF THE PREFERRED EMBODIMENT

Figure 1:
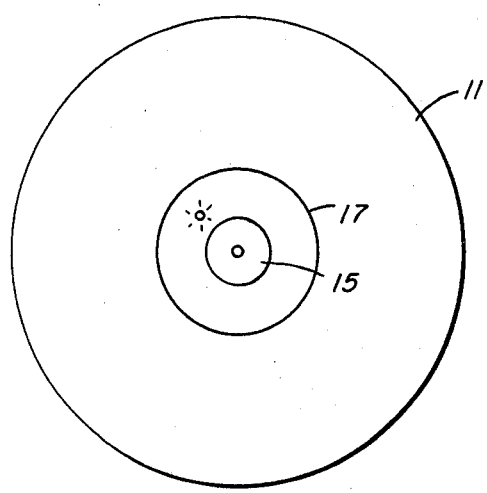
FIG. 1 is a front face view of a solid state sensor employed in an oxygen sensing system of the present invention.
Figure 2:
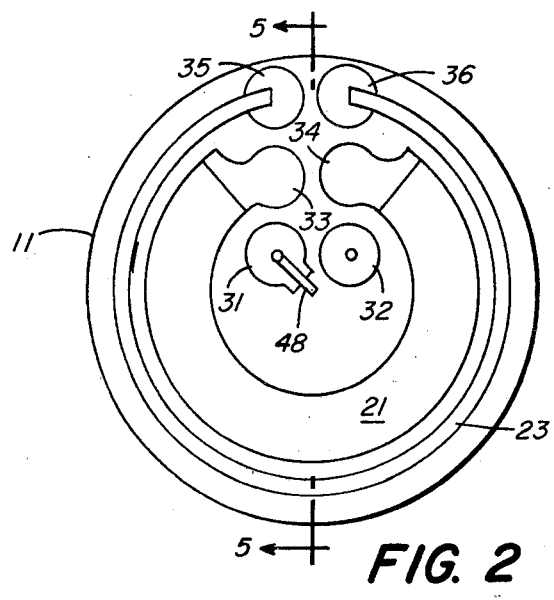
FIG. 2 is a back view of the sensor of FIG. 1.

Referring now to FIG. 1, the sensing portion of the system employs a thin, flat substrate 11, the front surface of which is adapted to contact the patient's skin. A preferred form of the substrate 11 is a thin disk of beryllium oxide. This disk may, for example, be of three-eighths inch diameter and 0.020 inch thick. The front face of the substrate carries a noble metal cathode 15 and a reference electrode 17. As described in greater detail hereinafter, electrodes 15 and 17 comprise a polarographic system for measuring the oxygen content of a patient's blood by the reduction of oxygen at the cathode 15. To improve stability of the polarographic electrode system, at least the front surface of the substrate, together with the electrodes 15 and 17, is covered by a very thin, oxygen-permeable polymer coating, formed in situ as described hereinafter.

A circular heating resistor 21 and an annular thermistor 23 are printed on the back of the substrate 11. Conductive pads 31-37 are provided for establishing electrical connection to these resistive elements, as well as to the electrodes 15 and 17 in a manner described hereinafter. Leads (not shown) are attached to the pads 31-36, e.g. by means of conductive epoxy, for connection to the control and measurement circuitry, also described hereinafter.

METHOD OF CONSTRUCTING THE OXYGEN SENSOR

Figure 3:
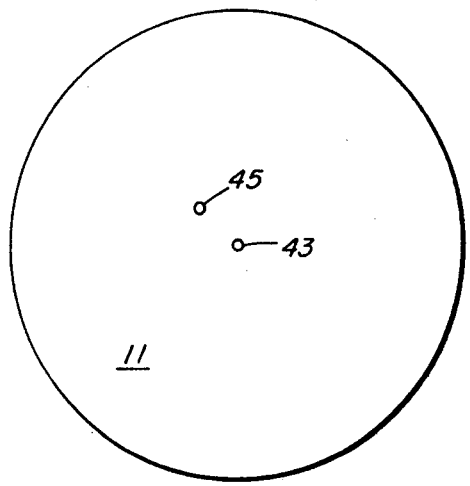
FIG. 3 is a front face view of a thin ceramic disk employed as a substrate in manufacturing the sensor of FIGS. 1 and 2.
Figure 4:
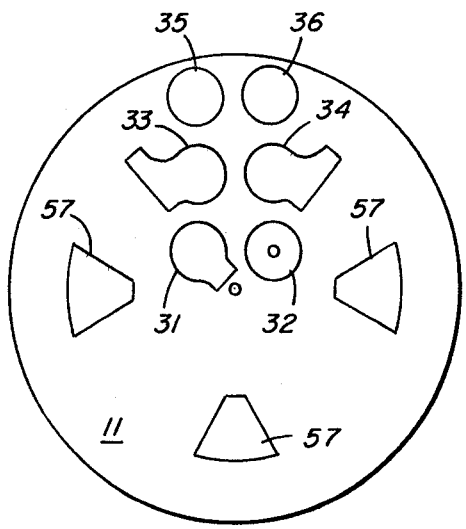
FIG. 4 is a back view of the substrate showing a pattern of conductive elements formed thereon as an early step in the manufacture of the sensor.

As indicated previously, a preferred form of the substrate 11 is a thin disk of beryllium oxide. Aluminum oxide is also suitable. Initially the disk is drilled, as indicated at 43 and 45 in FIG. 3, to provide an aperture (43) through which the noble metal cathode can pass and an aperture (45) facilitating connection to the reference electrode 17. Various conductive elements are then formed on the back surface of the substrate by conventional hybrid circuit construction techniques. In the embodiment shown, these conductive elements include the connection pads 31-36 and a series of wedge-shaped elements 57 which underlie portions of the heating resistor 21. A suitable paste or ink for forming the pads 31-36 and the wedges 57 is ESL-9630 manufactured by ElectroScience Labs. This paste is applied in the desired pattern by conventional screening techniques. After the pattern has been screened onto the back surface of the substrate, it is dried for approximately fifteen minutes at 125° and then fired at 1000° C. for twenty minutes to cure the conductive paste.

After the conductive elements have been applied to the back surface of the substrate, the heater element 21 and the thermistor element 23 are screened onto the backside of the substrate. The presently preferred material for this paste or ink is ESL-2612, again a product manufactured by ElectroScience Labs. This is a thermistor paste, i.e. a composition whose resistance changes significantly with temperature. By constructing the heater of such a composition, it can be employed in a self-sensing feedback control circuit and the thermistor 23 can be used for independent temperature measurement, if desired. Alternately, the separate, though integral, thermistor 23 can be used as the sensing element in the temperature controller. After screening with the thermistor paste, the substrate is dried for fifteen minutes at 125° C. and then fired for 875° C. for twenty minutes.

The purpose of the conductive wedges 57 which underlie the resistive heater 21 is to shunt a portion of the resistive current path near the outer circumference of the circular pattern and thereby reduce the radial nonuniformity of current distribution in the heater.

After the heater and thermistor elements have been formed, the reference electrode 17 is screened onto the front surface. A paste suitable for thick film printing techniques is prepared incorporating particles of both silver and silver-chloride, together with a fusible glass frit. Silver and silver-chloride powders are mixed in a ratio of about three parts silver to one part silver-chloride. Though this ratio is preferred based on present knowledge, no great criticality has been found. Rather, the process seems relatively tolerant and insensitive to minor variations so that large scale manufacturing is practical. The particle size of all components is about 30 microns. The silver and silver-chloride powders are obtained from EMCA of Mamaroneck, N.Y. Two forms of the powders are available. A so-called low surface area type in which the particles are essentially spherical and a high surface area type in which the particles are more plate-like. While both types are satisfactory, the high surface area is presently believed preferable.

Lead borosilicate glass frit or powder is then mixed in to comprise approximately 5% of the mixture by volume. The glass frit is also obtained from EMCA. A conventional pine oil/ethyl cellulose vehicle is then added to the mixture to form a paste suitable for conventional thick film screening or printing techniques, the amount of vehicle being adjusted to obtain a desirable viscosity. Typically, the resultant ink will have a solids content of about 80% by weight and a viscosity of approximately 150,000 centipoise. As will be understood by those skilled in the art, the vehicle is driven off before fusing of the frit and forms no part of resultant thick film.

After the reference electrode pattern is screened onto the substrate using the paste or ink described above, the substrate is dried for fifteen minutes at 125° C. to drive off the vehicle prior to firing and then fired at 500° C. for fifteen minutes. The firing process itself fuses the glass frit, binding the chemically active elements in the mixture to the substrate. Though the pattern overlies the aperture 45, the material is not caused to clog this opening or, if it is, the opening is subsequently mechanically reopened. As is conventional in the thin film and hybrid circuit manufacturing arts, the sequence of screening and firing steps is performed so that the progression is from higher firing temperatures to the lower firing temperatures.

Figure 5:
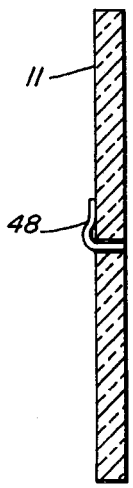
FIG. 5 is a side view, in section, of the sensor, taken substantially on the line 5—5 of FIG. 2.

To form the cathode 15, a short length of three mil. gold wire 48 is bent at essentially right angles. One arm of the right angle is passed through the center hole 43 with the orthogonal portion coming to rest on the conductve pad 31 where it is secured with the conductive epoxy (FIG. 5). The same conductive epoxy may be used to fill the hole 45 establishing a connection between the pad 32 and the reference electrode 17 on the front surface of the substrate. After the epoxy is cured, the wire which will form the cathode is sealed within the hole 43. A suitable material for this is a polyester resin such as Clear Cast. The portion of the gold wire protruding beyond the front surface of the substrate is then shaved off with a sharp scalpel to provide a fresh anodic surface.

After the printed circuit steps are completed, short leads are connected to the various pads 31–36 by means of conductive epoxy and these leads terminate in a connector suitable for electrically coupling the sensor to the control and measurement electronics described hereinafter.

Figure 6:
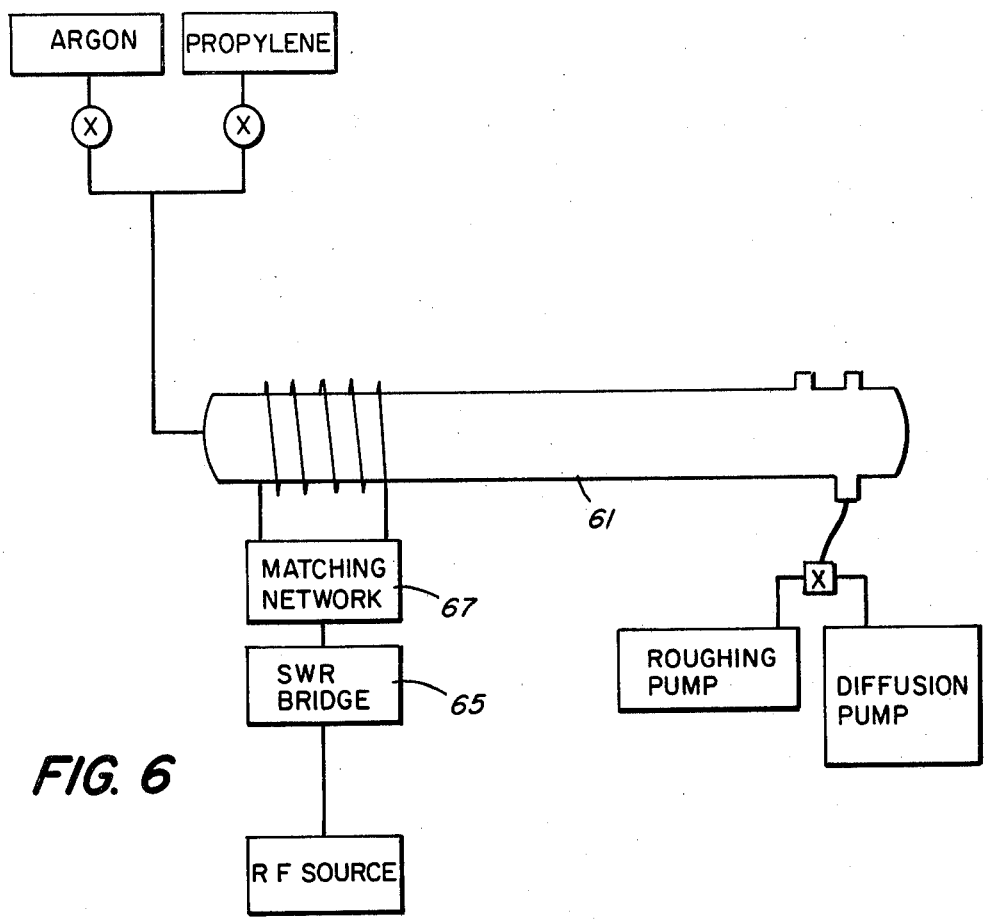
FIG. 6 is a diagram of an r.f. plasma polymerization apparatus employed in forming an in situ coating on the sensor of FIGS. 1 and 2.

The protective coating, described earlier as being applied over at least the front surface of the substrate 11, is formed in situ by plasma polymerization. After the reference electrode has been formed and the cathode has been sealed in the opening 43 and shaved flush with the face of the substrate, the substrates are placed in a vacuum chamber for the plasma forming process. In one particular implementation, illustrated in FIG. 6, a glass tube 61 about 75 millimeters in diameter and 100 centimeters long was utilized as the vacuum chamber. One end was connected to a vacuum pumping system and an r.f. coil 63 was placed around the other end. Provision was made at the end adjacent the coil for the bleeding in of selected gases.

In one particular device utilized, the coil was energized at 13.56 megahertz with about 100 watts of power. A conventional diathermy r.f. generator was used to power the coil through a conventional standing wave bridge 65 and matching network 67.

Substrates to be coated are placed within the tube 67 on glass slides. The vessel was then closed and evacuated to a pressure of about one micron. To effect cleaning and outgasing, an argon plasma is initially used. An argon flow of about 2.5 ccs per minute was introduced in the tube adjacent the RF zone, the pressure being held at about 35 microns. This condition is maintained for about 20 minutes.

Following the cleaning and after allowing the argon to be purged from the system, propylene monomer gas is bled into the system adjacent to the r.f. zone at a flow of about 0.75 sccm, yielding a pressure of about 6 microns. As is understood by those skilled in the art, the plasma discharge, created in the gas by the applied r.f. energy, creates bonding sites and permits an in situ r.f. energy polymerization of the monomer gas causing an intimate and tightly bonded coating to be formed on surfaces within the tube. With the particular apparatus utilized, the presently preferred coating is about 1.5 micrometers thick and is produced by operating the coating process for about 140 minutes.

Though operated in a heated mode, the sensor illustrated in FIG. 1 has a low enough power consumption that a feedback-controlled energizing circuit for the heater and calibrated polarographic current measuring circuit can all be battery operated and still provide a quite compact and portable unit. Suitable circuitry is described in the previously identified copending application of Gregory Zick.

In contrast with electrodes formed by in situ chloridating processes, the electrodes formed in accordance with the practice of the present invention have exhibited great stability. This stability has essentially obviated any need for preconditioning the electrode before use and has made feasible a pre-calibrating of sensors incorporating the electrode. Further, the method of manufacture lends itself to relatively large scale production techniques so that a single-use or throw-away type sensor is practical.

In view of the foregoing, it may be seen that several objects of the present invention are achieved and other advantageous results have been attained.

As various changes could be made in the above constructions without departing from the scope of the invention, it should be understood that all matter contained in the above description or shown in the accompanying drawings shall be interpreted as illustrative and not in a limiting sense.

We claim:

1. A solid state sensor for measuring the oxygen of blood by contact with a patient's skin, said sensor comprising:
   a thin ceramic substrate disc having front and back surfaces;
   a noble metal cathode, extending through said substrate from the back surface to the front surface where, at a first limited area of said front surface, said cathode is exposed for reducing oxygen; and
   a reference electrode comprising a mixture of silver, silver chloride and a fused glass frit forming a conductive film coating over a second limited area of said disc front surface.

2. The solid state sensor of claim 1 additionally comprising a heating element printed onto a first limited area of said back surface as a coating of resistor material.

3. The solid state sensor of claim 2 additionally comprising a thermistor printed onto a second limited area of said back surface.

4. The solid state sensor of claim 3 wherein said heating element and said thermistor are annular-shaped coatings on said back surface.

5. The solid state sensor of claim 1, 3 or 4 wherein said front surface is covered with an oxygen-permeable polymer coating.

6. The solid state sensor of claim 1, 3 or 4 wherein said reference electrode is an annular-shaped area of a film of said mixture.

7. The solid state sensor of claim 1, 3 or 4 wherein at least one of said silver and silver chloride are in the form of plate-like particles.

* * * * *